United States Patent [19]

Mangurten et al.

[11] 4,298,011
[45] Nov. 3, 1981

[54] BLOOD SAMPLE COLLECTOR

[76] Inventors: Henry H. Mangurten, 1640 Barry La., Glenview, Ill. 60025; Chester F. Vanek, 6812 Charlotte, Crystal Lake, Ill. 60014

[21] Appl. No.: 73,232

[22] Filed: Sep. 7, 1979

[51] Int. Cl.³ .............................................. A61B 5/14
[52] U.S. Cl. .................................... 128/763; 128/767; 128/771; 435/294
[58] Field of Search ............................... 128/763–767, 128/771, 272.1, DIG. 28, 276, 278; 435/294

[56] References Cited

U.S. PATENT DOCUMENTS

| 2,940,448 | 6/1960 | Furlong, Jr. | 128/766 |
| 3,175,553 | 3/1965 | Mattson | 128/771 X |
| 3,322,114 | 5/1967 | Portnoy et al. | 128/765 |
| 3,640,267 | 2/1972 | Hurtig et al. | 128/771 X |
| 3,926,521 | 12/1975 | Ginzel | 128/763 X |
| 4,065,360 | 12/1977 | Kreb | 128/765 X |

FOREIGN PATENT DOCUMENTS 683602  4/1964  Canada ................................. 128/763

Primary Examiner—Lee S. Cohen
Attorney, Agent, or Firm—S. J. Lehrer; William F. Frank

[57] ABSTRACT

A collector of a blood sample from a body member comprising a hollow container which is closed at both ends and has a hypodermic needle projecting from one of the ends and extending into the interior of the container. An arcuate disc of a frangible, inert material is sealingly positioned within the container to divide it into two compartments, one containing a blood culturing medium, the other air. An elongated tube engages the interior end of the needle and passes through the disc into the air chamber. When the wall of the container is deflected inwardly to expel the air to create a negative pressure condition within the container, the disc is broken thus allowing the blood drawn into the container when the wall is released to mix with the medium.

5 Claims, 3 Drawing Figures

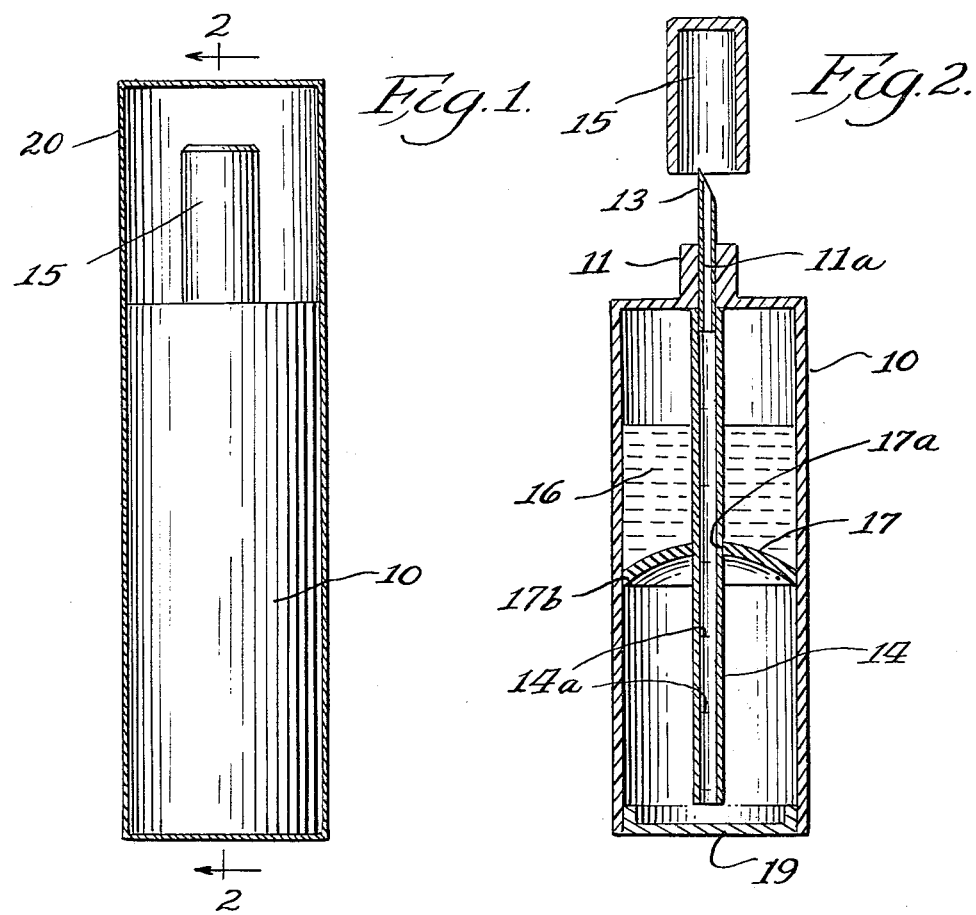
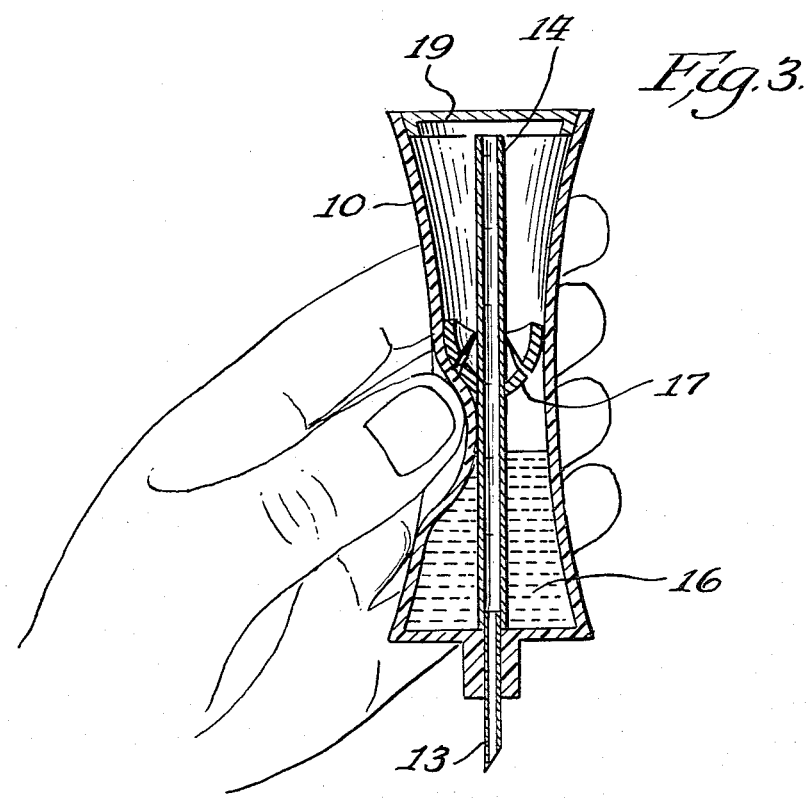

BLOOD SAMPLE COLLECTOR

Our investigation relates to the practice of drawing blood samples from very small or premature infants where infection is present or suspected. In such cases an intravenous approach could be difficult or hazardous; and the practice has been to obtain the sample by making a small skin puncture, usually in the heel of the infant. One method is to use a tiny blade in this manner to procure a droplet of blood. A collector similar to an eye-dropper is then applied to pick up the droplet. Usually the collector is a narrow tube which receives a tight-fitting rubber bulb at one end, and has a mark near such end as a limit for the blood sample drawn into the tube. Then the blood sample is ejected into a sterile test tube containing a culture medium suitable for testing the blood sample bacteriologically.

While the above method of obtaining the blood sample is generally satisfactory, it is quite involved, consumes time, and risks contamination. The parts are separately located, require delicate handling, and are apt to come in contact with unclean surfaces or objects, lending an unsanitary aspect to the process and the realization that it falls short of the high sanitation standards required for taking blood samples from very small or premature infants, particularly for bacteriological studies.

In view of the above situation, one object of the present invention is to provide a blood sample collector in the form of an instrument which accomplishes the necessary functions by direct application, in a brief period of time, and with a minimum of effort.

A further object is to design the collector with sterile areas on the inside for blood passage, in order to prevent contamination thereof, and cause no concern in this respect as the collector is handled on the outside.

Another object is to provide a collector which accomplishes all the functions mentioned in a simple instrument which is compact, easily handled, and of a nature to be produced at low cost.

A final and significant object of this collector is to provide a method of obtaining blood with minimal or no exposure to air. Since some significant bacteria grow only in a low-oxygen environment, this method would enhance the likelihood of accomplishing the diagnosis of such infections.

A better understanding of the invention may be gained by reference to the accompanying drawing, in which FIG. 1 is an enlarged section of the collector in upright position, as encased in a wrapper shown in section;

FIG. 2 is a section on the line 2—2 of FIG. 1, with a top cap and the wrapper removed; and FIG. 3 is a partial duplication of FIG. 2 inverted.

Referring specifically to the drawing, 10 denotes the most prominent part of the collector as an upright container of transparent plastic material and preferably round in form. Also, the wall of the container is flexible in order that it may be squeezed between the fingers as seen in FIG. 3. As shown in FIG. 2, the top of the container is closed, and rises with a neck 11 which has a central bore 11a providing a passage into the container. A hypodermic needle 13 is tightly fitted in the bore 11a, the outer end of the needle being pointed; and the inner end thereof projects a short distance into the container to receive the tightly-attached upper end of a transparent plastic tube 14, the latter extending down to terminate short of the lower end of the container, as shown in FIG. 2. The tube 14 is marked with a series of graduations 14a. The container receives a cap 15 fitted with pressure on the neck 11 to protect the pointed end of the needle from injury or contamination.

The construction of the collector is completed by first inverting it from the position of FIG. 2. Now the container first receives a partial filling of a liquid culture medium 16, then a saucer-shaped or arcuate disc 17 made of a brittle inert material, such as a hard wax. The disc has a center opening 17a and a circular rim 17b, securing a fit with the center tube 14 and the wall of the container, respectively, as the disc is inserted to the depth noted in FIG. 2. Finally, the open—now the top—end of the container receives a closure cap 19 of the simple form shown with a sealing fit; or, the cap may be a screw type. The collector is now a completed article, ready for use.

The collector is designed to be available in the medical supply department of a hospital or laboratory; and it comes sealed in a sterile wrapper 20 which is removed when the collector is to be used. For this purpose the cap 15 is first removed from the upright container as seen in FIG. 2. It will be recalled that the described parts accomplish separately, after the incision is made, the drawing of the blood droplet into a tube, and the transfer of the blood into the culture medium. These operations are combined more efficiently in the present collector because of its unique construction and operation. Thus, the first step in the use of the collector after inverting it as described with the needle point down is to make the incision in the heel of the infant. This brings a blood droplet to its surface.

The second step—as with an eye-dropper—is to squeeze the container as seen in FIG. 3 and force air out through the center tube 14 and the needle 13. However, a companion operation occurs in the present collector as this is done. Primarily, the disc 17 isolates the culture medium from the now upper chamber of the container, whatever the position of the collector may be. Thus, the culture medium will not flow into the chamber when the container is not in use or first handled, and leak out of the needle. However, this safeguard is unnecessary when the collector has been inverted, since the partial culture medium will rise only slightly when the container is squeezed. Also, the disc 17 will break as seen in FIG. 3 as soon as the squeezing commences. Now air compressed above the culture medium will rise through the broken disc and add pressure to the flow of air through the tube 14 and needle 13.

After the above step the collector—with the container still squeezed—may be lowered to engage the needle with the blood droplet. Next, the release of the squeezing pressure will draw the blood through the needle and tube to overflow the latter and drop through the broken disc 17 into the culture medium below. Now, or at such time as a sample of the culture is needed, the tilting of the collector to horizontal position will induce a desired supply of the culture medium to flow into the tube and out of the needle.

Probably, the needle would serve equally well—if lengthened—without the plastic tube 14. However, the proper quantity of the culture medium may vary for different tests. Therefore, the tube graduations will serve for filling the container accordingly. Actually, the main purpose of the graduations is to determine the amount of blood collected.

It will now be apparent that the present collector combines all the operations mentioned in a single instrument, usable in the one inverted position after the needle has been exposed. Further, when so held no other manual access is necessary to any part with the risk of contamination. Further, the container neck 11 serves as a stop in case the needle is advanced further than necessary for making the incision. Finally, the collector is suitable for manufacture at low cost and under the highest sanitary conditions, and would best be discarded after its original use in keeping with that requirement.

We claim:

1. A disposable blood sample collector comprising a cylindrical container having an integrally formed end wall at one end and an open other end, a closure closing the other open end, a disc of frangible inert material sealingly positioned within said container dividing said container into one portion as a chamber containing a blood culture medium and a second portion as an air chamber, a hypodermic needle extending through said end wall communicating the exterior of the container with said one portion, an elongated tube tightly fitted to said needle extension within said container and extending axially therewithin through said disc and communicating with said second portion, the container wall being flexible for deflection inwardly to expel air from said one portion and to return to cylindrical form when released, the needle adapted to engage the blood sample to draw the sample into said air chamber.

2. The structure of claim 1, said tube being marked with graduations to indicate the amount of blood collected.

3. The structure of claim 1, said disc being arcuate.

4. The structure of claim 1 wherein a neck extends outwardly from said end wall and surrounds a portion of said needle.

5. The structure of claim 4 wherein a protective, removable cap is fitted on said neck and encloses said needle.

* * * * *